United States Patent [19]

Grassetti

[11] 4,152,439

[45] May 1, 1979

[54] STIMULANT AND ANTIDEPRESSANT AGENTS

[75] Inventor: Davide R. Grassetti, 26 Northgate Ave., Berkeley, Calif. 94708

[73] Assignees: Davide R. Grassetti; Mine E. Grassetti, both of Berkeley, Calif.

[21] Appl. No.: 868,731

[22] Filed: Jan. 12, 1978

[51] Int. Cl.² .......................................... A61K 31/455
[52] U.S. Cl. .................................................. 424/266
[58] Field of Search ........................................ 424/266

[56] References Cited

PUBLICATIONS

Chemical Abstracts 81: 20649u, (1974).

*Primary Examiner*—Jerome D. Goldberg

[57] ABSTRACT

It has been discovered that administration to human subjects of an effective dosage of a non-toxic dithiobisheterocyclic compound, such as 6,6'-dithiodinicotinic acid, causes an increased sense of well-being and hyperactivity, without any obvious neurological findings or other undesirable side-effects.

3 Claims, No Drawings

STIMULANT AND ANTIDEPRESSANT AGENTS

It has been discovered that administration of 6,6'-dithiodinicotinic acid to human subjects causes an enhanced sense of well-being and hyperactivity.

6,6'-Dithiodinicotinic acid belongs to a group of dithiobisheterocyclic compounds which are capable of reacting with the external sulfhydryl groups of cells in such a manner as to modify the cell surface charge, blocking the external sulfhydryl groups at the same time.

Their general formula can be represented as follows:

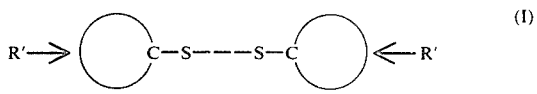
(I)

wherein the R's, which may be the same as or different from one another, represent heterocyclic radicals containing from 1 to 5 ring nitrogen atoms and optionally sulfur in the ring, along with carbon. Said radicals may be substituted or unsubstituted, and can represent single or fused aromatic rings.

The presence of pyridyl nuclei substituted by anionic groups (or potential anionic groups as in the ester) makes these compounds essentially non-toxic by preventing or greatly diminishing their ability to enter inside mammalian cells.

The compounds in this preferred group have one or the other of the structures.

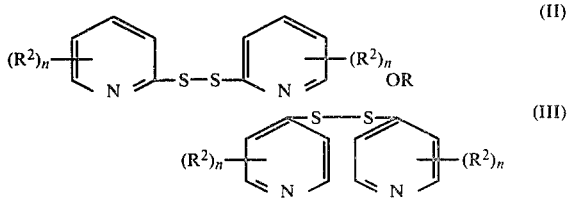

wherein n represents a whole integer having a value of from 1 to 4, and the $R^2$s represent carboxy groups or the salt, ester or amide derivatives of said carboxy groups. For example, suitable salts are those formed with alkali or alkaline earth metals, with ammonia or with amines such as cyclohexylamine, morpholine or other aliphatic, alicyclic, aromatic or heterocyclic amines. Representative ester moieties are those such as methyl, ethyl and higher alkyl groups, as well as cyclohexyl and other alicyclic groups. Representative amide groups for substitution on the pyridyl nuclei include —$CONH_2$, as well as those wherein one or both hydrogen atoms on the amide nitrogen atom are replaced by aliphatic, heterocyclic, alicyclic or aromatic groups, including those of a substituted character; typical groups are beta-aminoethanol and morpholine.

Representative compounds coming within the group represented by structures (II) or (III) above include: 4,4'-dithiodinicotinic acid, 6,6'-dithiodinicotinic acid, 2,2'-dithiodinicotinic acid, 2,2'-dithiobis-(isonicotinic acid), 6,6'-dithiodipicolinic acid, 4,4'-dithiodipicolinic acid, 4,4'-dithiodinicotinic acid sodium salt, 6,6'-dithiodinicotinic acid sodium salt, 2,2'-dithiodinicotinic acid sodium salt, 6,6'-dithiodipicolinic acid sodium salt, 2,2'-dithiobis-(isonicotinic acid) sodium salt, 6,6'-dithiodinicotinic acid potassium salt, 6,6'-dithiodinicotinic acid magnesium salt, 6,6'-dithiodinicotinic acid ammonium salt, 6,6'-dithiodinicotinic acid lithium salt, 4,4'-dithiodipicolinic acid potassium salt, 4,4'-dithiobis (2,5-pyridinedicarboxylic acid), 4,4'-dithiobis-(2,6-pyridinedicarboxylic acid), 2,2'-dithiobis-(3,4-pyridinedicarboxylic acid,), 4,4'-dithiobis-(3,5-pyridinedicarboxylic acid), 4,4'-dithiobis-(2,6-pyridinedicarboxylic acid sodium salt), 4,4'-dithiobis-(2,3,5-pyridinetricarboxylic acid), 2,2'-dithiobis-(3,4,5-pyridinetricarboxylic acid) and 2,2'-dithiobis-(3,4,5,6-pyridinetetracarboxylic acid).

Good results can also be obtained with compounds having the structure of II or III above, except that the pyridyl rings are substituted by —$CH_3$ or other alkyls, OH, CN, halogen or —CNO. The —COOH or derivative groups thereof can also be present on the ring, if desired.

All the foregoing compounds corresponding to the II or III structure are capable of reacting with a sulfhydryl group to form a thione product, said compounds thus being referred to as "thione-forming" reagents.

The following Examples demonstrate the lack of toxicity of these compounds to animals and humans, and their effectiveness as stimulant and antidepressant agents.

EXAMPLE 1

Each of 6 healthy mice, were injected intraperitoneally with 18 mg per day of 6,6'-dithiodinicotinic acid sodium salt for 18 consecutive days, equivalent to a daily dosage of 450 mg per kilo of body weight. The injected chemical was dissolved in aqueous buffer, pH 7.2. The mice were very active and exhibited no adverse effects. Their appetites remained good and no weight loss was suffered.

EXAMPLE 2

The chemical 6,6'-dithiodinicotinic acid was injected into Swiss mice for prolonged periods of time and at high dosage levels to determine its toxicity to mice. The details of this work, together with the results thereof showing non-toxicity, are fully set forth in the following Table 1:

TABLE 1

TOXICITY OF 6,6'-DITHIODINICOTINIC ACID TO SWISS MICE
INJECTIONS TOTAL DAILY DOSE (mg)

| Number of mice | Number* of daily injections | Dose per injection (mg) | Per mouse (mg) | Per kilo (mg) | DURATION OF EXPERIMENT | VISIBLE EFFECT |
|---|---|---|---|---|---|---|
| 6** | 2 | 6 + 12 | 18 | 450 | 21 days | None |
| 13*** | 3 | 4 + 4 + 4 | 12 | 600 | 11 days | None |
| 18**** | 3 | 6 + 6 + 6 | 18 | 900 | 13 days | None |
| 5 | 1 | 20 | 20 | 1,000 | Single | None |

TABLE 1-continued

TOXICITY OF 6,6'-DITHIODINICOTINIC ACID TO SWISS MICE
INJECTIONS TOTAL DAILY DOSE (mg)

| Number of mice | Number* of daily injections | Dose per injection (mg) | Per mouse (mg) | Per kilo (mg) | DURATION OF EXPERIMENT | VISIBLE EFFECT |
|---|---|---|---|---|---|---|
| | | | Injection | | | |

6,6'-Dithiodinicotinic acid was neutralized with equimolar amount of Na Bicarbonate for injection. The concentration was such that the injected volume was 0.1 ml or 0.2 ml per injection. All injections were intraperitoneal.
*When 2 daily injections were given, the times were 8 AM and 4 PM; when 3 daily injections were given, the times were 8 AM, 12 Noon, and 4 PM.
**This group consisted of 40-gram, female swiss mice. Injections on 21 consecutive days.
***This group consisted of 20-gram Swiss mice, 11 females and 2 males. The injections were given over a period of 13 days, daily except weekends and holidays.
****This group consisted of 20-gram Swiss mice, 16 females and 2 males. The injections were given daily over a period of 21 days, daily except weekends and holidays.

EXAMPLE 3

Toxicity of Diethyl Ester of 6,6'-dithiodinicotinic acid

When administered as an aqueous or oily (sesame oil) suspension subcutaneously to Swiss mice, the compound, which is very insoluble in water, did not spread systemically, but tended to incapsulate in situ.

Oral administration in food

Mouse chow was ground up and mixed with distilled water (0.8 ml water/gram food); the compound was finely ground and thoroughly mixed to this chow. It was determined that, on the average, each mouse used 3 grams of food per day. Mice used were Swiss Webster, 18-20 grams.

| Group | No. mice | Conc. in food | Daily dose per mouse | Daily dose per kilo | Duration (days) | Visible Effects |
|---|---|---|---|---|---|---|
| 1 | 25 | 4 mg/g | 12 mg | 600 mg | 8 | None |
| 2 | 25 | 6 mg/g | 18 mg | 900 mg | 8 | None |

EXAMPLE 4

A cat, age 20 years, weight 8 pounds, suffering from squamous cell carcinoma, (as demonstrated by histological diagnosis) was given 100 mg of 6,6'-dithiodinicotinic acid twice daily orally in his milk. This treatment was continued for 14 days without any ill effects being noticed. The cat survived at least one month after receiving the last dose of the compound.

EXAMPLE 5

To establish the safety of 6,6'-dithiodinicotini acid for use in a living mammal, the effect of this chemical on the aggregation of human blood platelets by ADP (adenosine diphosphate) was studied. The details of this study, together with the results thereof showing the 6,6'-dithiodinicotinic acid to be without effect on this blood-clotting function, are presented in the following Table 2;

TABLE 2

EFFECT OF 6,6-DITHIODINICOTINIC ACID ON THE AGGREGATION OF HUMAN BLOOD PLATELETS BY ADENOSINE DIPHOSPHATE

| Conc. of ADP | Conc. of CPDS | O.D. before addition of ADP | O.D. after addition of ADP at different times | | | | Effect of CPDS |
|---|---|---|---|---|---|---|---|
| | | | 1 min. | 2 min. | 3 min. | 4 min. | |
| None | None | 0.74 | 0.75 | 0.76 | 0.76 | 0.76 | |
| None | $10^{-3}$M | 0.75 | 0.76 | 0.76 | 0.76 | 0.76 | None |
| $10^{-4}$M | None | 0.76 | 0.34 | 0.27 | 0.25 | 0.23 | |
| $10^{-4}$M | $10^{-3}$M | 0.76 | 0.34 | 0.29 | 0.25 | 0.23 | None |
| $10^{-5}$M | None | 0.78 | 0.42 | 0.32 | 0.29 | 0.26 | |
| $10^{-5}$M | $10^{-3}$M | 0.77 | 0.43 | 0.34 | 0.33 | 0.30 | None |
| $10^{-6}$M | None | 0.75 | 0.45 | 0.36 | 0.33 | 0.30 | |
| $10^{-6}$M | $10^{-3}$M | 0.76 | 0.48 | 0.40 | 0.36 | 0.35 | None |

Abbreviations: ADP = adenosine diphosphate; O.D. = optical density; CPDS = 6,6'-dithiodinicotinic acid
Procedure. Human blood (18 ml) was mixed with sodium citrate dihydrate (70 mg in 2 ml) immediately upon drawing. It was centrifuged at 2°-4° at 1,000 RPM for 2 minutes, the top layer of the platelet-rich plasma (PRP pipetted off and kept in ice.) Centrifugation and pipetting of PRP was repeated 5 times, giving a total of 10 ml PRP, which was diluted to 35 ml with isotonic saline. The procedure for determining the aggregation of platelets from the decrease of the optical density was that of G. Zbinden, J. N. Mehrishi, and S. Tomlin, Thromb. Diath. Haem. 23, 261 (1970). Siliconized glass matched colorimeter tubes were used, in a Bausch & Lomb Spectronic 505 recording spectrophotometer, set at 610 nm. Samples of 3.3 ml of PRP were used; they were allowed to warm up to room temperature, then ADP (various amounts in 1χ or 10λ of solution) was added, the tube tapped forcefully for 1 minute, and the optical density measured every minute for 4 minutes after tapping. A parallel series was run by incubating PRP with CPDS ($10^{-3}$M final conc.) for 5 minutes at room temperature, then adding ADP as described.

EXAMPLE 6

6,6'-dithiodinicotinic acid was administered orally to a healthy, 48-year old female, with the following schedule:

Day 1—10 AM—600 mg
10 PM—600 mg
Day 2—10 AM—600 mg
Day 3—10 AM—300 mg
Day 4—10 AM—300 mg
Day 6—10 AM—150 mg

Various blood determinations were made on Day 0, before beginning administration of the compound, and on Day 3, two hours after the morning dose of the compound, when the stimulating and antidepressant effects were high. No abnormal findings were made in the blood analyses (see Table 3). Physical examination by a physician revealed no abnormality, and no obvious neurological effects.

EXAMPLE 7

6,6'-dithiodinicotinic acid was administered orally to a healthy 56-year old male, with the same schedule as in Example 6. An increased sense of well-being and hyperactivity were experienced. The results of blood analyses on day 0 and on day 3 (two hours after the daily dose) are reported in Table 4. No abnormal findings were made in the blood, or in the physical examination by a physician.

Table 3

| | | Day 0 | | | |
|---|---|---|---|---|---|
| Test No. | Test Description | Results | Units | Normal Adult Values | |
| 600 | GLUCOSE | 76 | MG/DL | 68–113 | T13 |
| 603 | UREA NITROGEN | 18.0 | MG/DL | 6.0–25.0 | T56 |
| 604 | URIC ACID | 5.0 | MG/DL | 2.5–7.5 | T56 |
| 605 | CHOLESTEROL | 205 | MG/DL | SEE REVERSE | T56 |
| 707 | CALCIUM | 9.5 | MG/DL | 8.4–10.6 | T<> |
| 608 | TOTAL BILIRUBIN | 0.6 | MG/DL | 0.4–1.4 | T56 |
| 610 | POTASSIUM | 4.2 | MEQ/L | 3.5–5.0 | T56 |
| 611 | SODIUM | 142 | MEQ/L | 135–150 | T56 |
| 612 | ALK. PHOSPHATASE | 54 | I.U. | 30–110 | T56 |
| 613 | TOTAL PROTEIN | 6.9 | GM/DL | 6.2–8.3 | T56 |
| 614 | ALBUMIN | 4.38 | GM/DL | 3.5–5.1 | |
| | GLOBULIN | 2.6 | GM/DL | 1.9–3.9 | |
| | A/G RATIO | 1.6 | | 1.0–2.2 | |
| 615 | PHOSPHORUS | 3.2 | MG/DL | 2.7–4.5* | T56 |
| 620 | SGOT | 18 | UV UNITS | 8–45 | T56 |
| 621 | LDH | 160 | MU/ML | 140–232 | T56 |
| 706 | SGPT | 14 | MU/ML | 3–40 | T<> |

| | | 3 | | | |
|---|---|---|---|---|---|
| Test No. | Test Description | Results | Units | Normal Adult Values | |
| 600 | GLUCOSE | 87 | MG/DL | 68–113 | T<> |
| 603 | UREA NITROGEN | 16.8 | MG/DL | 6.0–25.0 | T05 |
| 604 | URIC ACID | 4.1 | MG/DL | 2.5–7.5 | T05 |
| 605 | CHOLESTEROL | 196 | MG/DL | SEE REVERSE | T05 |
| 707 | CALCIUM | 9.5 | MG/DL | 8.4–10.6 | T<> |
| 608 | TOTAL BILIRUBIN | 0.5 | MG/DL | 0.4–1.4 | T05 |
| 610 | POTASSIUM | 4.7 | MEQ/L | 3.5–5.0 | T05 |
| 611 | SODIUM | 143 | MEQ/L | 135–150 | T05 |
| 612 | ALK. PHOSPHATASE | 56 | I.U. | 30–110 | T05 |
| 613 | TOTAL PROTEIN | 7.2 | GM/DL | .6.2–8.3 | T05 |
| 614 | ALBUMIN | 4.29 | GM/DL | 3.5–5.1 | |
| | GLOBULIN | 3.0 | GM/DL | 1.9–3.9 | |
| | A/G RATIO | 1.4 | | 1.0–2.2 | T05 |
| 615 | PHOSPHORUS | 3.5 | MG/DL | 2.7–4.5 | T05 |
| 620 | SGOT | 27 | UV UNITS | 8–45 | T05 |
| 621 | LDH | 162 | MU/ML | 140–232 | T05 |
| 706 | SGPT | 14 | MU/ML | 3–40 | T<> |

Table 4

| | | Day 0 | | | |
|---|---|---|---|---|---|
| Test No. | Test Description | Results | Units | Normal adult values | |
| 600 | GLUCOSE | 82 | MG/DL | 68–113 | T<> |
| 603 | UREA NITROGEN | 12.1 | MG/DL | 6.0–25.0 | T56 |
| 604 | URIC ACID | 5.4 | MG/DL | 2.5–7.5 | T56 |
| 605 | CHOLESTEROL | 213 | MG/DL | SEE REVERSE | T56 |
| 707 | CALCIUM | 9.5 | MG/DL | 8.4–10.6 | T<> |
| 608 | TOTAL BILIRUBIN | 0.5 | MG/DL | 0.4–1.4 | T56 |
| 610 | POTASSIUM | 4.5 | MEQ/L | 3.5–5.0 | T56 |
| 611 | SODIUM | 143 | MEQ/L | 135–150 | T56 |
| 612 | ALK, PHOSPHATASE | 91 | I.U. | 30–110 | T56 |
| 613 | TOTAL PROTEIN | 7.4 | GM/DL | 6.2–8.3 | T56 |
| 614 | ALBUMIN | 4.76 | GM/DL | 2.5–5.1 | |
| | GLOBULIN | 2.7 | GM/DL | 1.9–3.9 | |
| | A/G RATIO | 1.7 | | 1.0–2.2 | T56 |
| 615 | PHOSPHORUS | 2.4 | *L MG/DL | 2.7–4.5* | T56 |
| 620 | SGOT | 25 | UV UNITS | 8–45 | T56 |
| 621 | LDH | 190 | MU/ML | 140–232 | T56 |
| 706 | SGFT | 19 | MU/ML | 3–40 | T<> |

| | | Day 3 | | | |
|---|---|---|---|---|---|
| Test No. | Test Description | Results | Units | Normal Adult Values | |
| 600 | GLUCOSE | 99 | MG/DL | 68–113 | T<> |
| 603 | UREA NITROGEN | 17.1 | MG/DL | 6.0–25.0 | T05 |
| 604 | URIC ACID | 5.1 | MG/DL | 2.5–7.5 | T05 |
| 605 | CHOLESTEROL | 210 | MG/DL | SEE REVERSE | T05 |
| 707 | CALCIUM | 9.1 | MG/DL | 8.4–10.6 | T<> |
| 608 | TOTAL BILIRUBIN | 0.4 | MG/DL | 0.4–1.4 | T05 |
| 610 | POTASSIUM | 4.1 | MEQ/L | 3.5–5.0 | T05 |
| 611 | SODIUM | 145 | MEQ/L | 135–150 | T05 |
| 612 | ALK. PHOSPHATASE | 95 | I.U. | 30–110 | T05 |

Table 4-continued

| 613 | TOTAL PROTEIN | 7.7 | GM/DL | 6.2-8.3 | T05 |
|---|---|---|---|---|---|
| 614 | ALBUMIN | 4.45 | GM/DL | 3.5-5.1 | |
| | GLOBULIN | 3.3 | GM/DL | 1.9-3.9 | |
| | A/G RATIO | 1.3 | | 1.0-2.2 | T05 |
| 615 | PHOSPHORUS | 2.3 | *L MG/DL | 2.7-4.5 | T05 |
| 620 | SGOT | 29 | UV UNITS | 8-45 | T05 |
| 621 | LDH | 165 | MU/ML | 140-232 | T05 |
| 706 | SGPT | 18 | MU/ML | 3-40 | T<> |

EXAMPLE 8

6,6'-dithiodinicotinic acid diethyl ester (150 mg) was administered orally to a 48-year old healthy female. The euphoric and stimulating effect began approximately two hours after administration. It was thus delayed as compared to the free 6,6'-dithiodinicotinic acid, which elicits those effects approximately 15 minutes after oral administration.

EXAMPLE 9

A female cancer patient, age 53, following surgery for ovarian carcinoma, was given chemotherapy treatment. She took 6,6'-dithiodinicotinic acid orally (300 mg daily, in two separate doses of 150 mg each) for a total of 100 days, at the present writing, and is continuing to take it. The patient feels that the drug gives her a sense of well-being, and makes her condition more bearable.

EXAMPLE 10

A male cancer patient, age 79, suffering from lung carcinoma, is taking 600 mg daily of 6,6'-dithiodinicotinic acid (two daily doses of 300 mg each, orally). He is regularly checked by his physician, and they both feel that the drug gives him a sense of well-being. He has taken the drug for 60 days and is continuing to take it.

The dosage rate of the dicyclic or other reagent to be employed in a practice of this invention can be varied within wide limits and still be effective for the intended purpose. In general, however, good results can be obtained by administering the reagent in amounts calculated to maintain a concentration in the blood of about $10^{-6}$ to about $10^{-3}$ molar.

The dicyclic or other reagents employed in the practice of this invention can be administered in any desired fashion, such, for example, as by injection into the blood stream or into muscle or body tissue. Oral administration is also effective, The chemical can be amployed per se or along with an oleaginous or other vehicle which will slow down its rate of absorption into the system.

I claim:

1. The method of producing an anti-depressant effect in a depressed human being which comprises administering to said human being an effective anti-depressant amount of a material selected from the group consisting of 6,6'-dithiodinicotinic acid, the ammonium or alkali metal salt of 6,6'-dithiodinicotinic acid and the lower akkyl ester of 6,6'-dithiodinicotinic acid.

2. The method of claim 1 wherein the amount of material administered is in the range about 150 to 600 mg per day.

3. The method of producing an anti-depressant effect in a depressed human being which comprises administering to said human being a material selected from the group consisting of 6,6' dithiodinicotinic acid, the ammonium or alkali metal salt of 6,6' dithiodinicotinic acid and the lower alkyl ester of 6,6' dithiodinicotinic acid in an amount sufficient to maintain a concentration of $10^{-6}$ to $10^{-3}$ molar in the blood.

* * * * *